United States Patent [19]

Osipow et al.

[11] Patent Number: 4,832,945

[45] Date of Patent: May 23, 1989

[54] DEODORANT STICK

[76] Inventors: lloyd I. Osipow, 2 Fifth Ave., New York, N.Y. 10011; Dorothea C. Marra, 107 Fernwood Rd., Summit, N.J. 07901; J. George Spitzer, 44 Coconut Row, Palm Beach, Fla. 33480

[21] Appl. No.: 867,515

[22] Filed: May 28, 1986

[51] Int. Cl.⁴ .................. A61K 7/32; A61K 7/36; A61K 7/38

[52] U.S. Cl. .................. 424/65; 424/DIG. 5; 424/67; 424/68

[58] Field of Search .............. 424/DIG. 5, 65, 68

[56] References Cited

U.S. PATENT DOCUMENTS

| 279,195 | 6/1883 | Slocomb et al. | 424/65 |
|---|---|---|---|
| 1,558,405 | 10/1925 | Smith | 424/65 |
| 4,126,679 | 11/1978 | Davy et al. | 424/66 |
| 4,414,200 | 11/1983 | Murphy et al. | 424/65 |
| 4,440,741 | 4/1984 | Marsehner | 424/DIG. 5 |
| 4,526,780 | 7/1985 | Marschner et al. | 424/65 |
| 4,548,808 | 10/1985 | Chankin | 424/DIG. 5 |
| 4,659,644 | 4/1987 | Cox et al. | 424/DIG. 5 |

FOREIGN PATENT DOCUMENTS

| 0120508 | 7/1982 | Japan | 424/DIG. 5 |
|---|---|---|---|
| 2026860 | 2/1980 | United Kingdom | 424/DIG. 5 |
| 2097673 | 11/1982 | United Kingdom | 424/DIG. 5 |

*Primary Examiner*—Dale R. Ore
*Attorney, Agent, or Firm*—Morgan & Finnegan

[57] ABSTRACT

An underarm deodorant suspensoid stick that is essentially free from any tendency to cause iritation is obtained by suspending in a gelled water-insoluble organic liquid powdered sodium bicarbonate having a particle size in the range of essentially 100% less than 44 micron and at least about 25% greater than 1 micron.

3 Claims, No Drawings

DEODORANT STICK

BACKGROUND

This invention is concerned with deodorant sticks. In the past, the prevalent deodorant stick consisted of ethyl alcohol gelled with sodium stearate and containing a small quantity of an alcohol-soluble antimicrobial agent and fragrance. These sticks were effective deodorants, but had the drawback of causing irritation due to the high concentration of alcohol.

Davy et al, U.S. Pat. No. 4,126,679 is concerned with cosmetic sticks that employ a combination of a powdered material suspended in a solid solution of volatile silicones and long chain alcohols. Cosmetic sticks corresponding in large measure to this invention are widely used as antiperspirants. As such, the powdered materials are zirconium and aluminum salts. Such antiperspirants are also effective deodorants. According to the Davy et al patent, sodium bicarbonate may be used as the powdered component of a stick composition.

However, it is known that stick antiperspirants can not be used by many people because they find them to be irritating. We have found that stick deodorants containing sodium bicarbonate, prepared in accordance with the Davy patent are also irritating.

OBJECTS OF THE INVENTION

An object of this invention is to provide an improved underarm deodorant stick. Another object of this invention is to provide an underarm deodorant stick which is virtually free from any tendency to cause irritation.

DESCRIPTION OF THE INVENTION

It has been discovered that deodorant stick compositions that are virtually free from any tendency to cause irritation can be prepared by dispersing powdered sodium bicarbonate of such size that virtually 100% passes through a 325 mesh sieve, and is therefore less than 44 micron, in vehicle comprising an anhydrous, water-insoluble organic liquid and a gelling agent.

This is a surprising discovery. Among water-soluble salts, it appears to apply only to sodium bicarbonate. For example, an impalpable grade of aluminum chlorhydrate was sieved and only the portion that passed through a 325 mesh sieve was incorporated in a volatile silicone-stearyl alcohol stick. The sticks were found to be irritating. The same results were obtained using sodium chloride in place of aluminum chlorhydrate, after grinding and passing through a 325 mesh sieve.

The explanation for the failure of fine particles to avoid irritation in the case of aluminum chlorhydrate and sodium chloride is quite simple. The amount of perspiration in the armpits varies throughout the day. Perspiration flows and water evaporates. Water-soluble salts deposited from an underarm stick will dissolve in the perspiration liquid and then crystallize out when water in the perspiration evaporates. It is well known that under these conditions the smallest particles will dissolve first and the larger particles will grow. After a short period under the arms, the particles have become large enough to scratch and irritate.

For reasons, about which the inventors can only speculate, this does not happen with sodium bicarbonate. With 10 to 20% of the particles retained on a 325 mesh sieve, sodium bicarbonate in a suspensoid stick does cause irritation, However, when these larger particles are eliminated before preparing the stick, irritation does not occur, likely explanations are that sodium bicarbonate either does not dissolve in or does not crystallize of liquid perspiration. With regard to the latter, since perspiration is acidic, any sodium bicarbonate that dissolves in the perspiration is converted to carbon dioxide and the sodium salt of the fatty acids present in perspiration and these salts do not crystallize onto bicarbonate crystals to add to their size. It is also possible that perspiration is a poor solvent for sodium carbonate.

There is a lower limit to particle size of the powdered sodium bicarbonate. If the particle size is too small, the stick will feel dry and it will exhibit drag rather then an easy glide when applied to the armpits. It is possible to counter-act the effect of the smaller particle size by using less sodium bicarbonate, but this results in reduced deodorant action. It has been found that the powdered sodium bicarbonate should have a particle size in the range of essentially 100% less than 44 microns and at least about 25% greater than 1 micron.

The deodorant sticks of this invention comprise in addition to sodium bicarbonate, a water-insoluble organic liquid and a gelling agent for that liquid.

The organic liquid should be essentially insoluble in water. That is, its solubility in water should be no more than about 1 or 2% by weight. If the organic liquid were soluble in water, it would take up water from a humid atmosphere. This would have an adverse effect on the stability of the sodium bicarbonate.

It is advantageous, but not essential, that all or part of the organic liquid should be volatile. The deodorant stick should impart a relatively dry feeling when applied to the underarms, and it should not stain the garments as a consequence of being excessively oily. These effects can be achieved, even without a completely volatile liquid carrier, if the stick is firm enough to avoid excessive transfer to the underarms, and the ratio of non-volatile liquid carrier to suspended particles is not too high. In general, this ratio should not exceed 2.5 to 1.0, and preferably, it should not exceed 2.0 to 1.0 by weight.

The volatile organic liquids that may be used include polydimethylcyclosiloxanes having 3 to 5 silicon atoms, linear polydimethylsiloxanes, and saturated aliphatic hydrocarbons, These volatile liquids should boil within the range of 300° F. to 500° F.

Nonvolatile organic liquids that may be used in the practice of this invention may be any of a large number of water-insoluble organic liquids that are used as emollients or carriers in cosmetic compositions. These include non-volatile silicone oils, mineral oils and vegetable oils, various esters, such as isopropyl myristate, butyl stearate, decyl oleate, lauryl lactate, and diisopropyl adipate, and ethers such as propoxylated cetyl alcohol and propoxylated myristyl propionate, The compositions may contain a mixture of volatile organic liquids or a mixture of non-volatile organic liquids or a mixture consisting of both volatile and non-volatile organic liquids, Preferably, at least about 25% by weight of the water-insoluble organic liquid should be volatile, In general, any of a variety of organic gelling agents of mixtures of gelling agents may be used in the practice of this invention, provided they produce a rigid gel, Suitable gelling agents include natural and synthetic waxes and the soaps of long-chain fatty acids. Examples of natural and synthetic waxes include: paraffin waxes, microcrystalline waxes, candelilla wax, spermacetti wax, ceresine, ozocerite, castor wax, glyceryl monostearate, stearyl alcohol, cetyl alcohol, polyethylene wax, and waxes that are copolymers of ethlene and vinyl acetate, Examples of soaps include aluminum distearate, sodium stearate and aluminum octoate.

The long-chain aliphatic alcohols having 16 to 22 carbon atoms are particularly advantageous gelling agents because they form sticks having superior glide. It is preferable that these long-chain alcohols constitute at least about 25% by weight of the gelling agent.

The compositions of this invention contain from about 10 to 40% by weight of sodium bicarbonate, with essentially 100% less than 44 microns and at least about 25% by weight larger than 1 micron, from about 10 to about 40% by weight of gelling agent, and from about 30 to about 80% by weight of water-insoluble organic liquid, In addition to the above essential ingredients, various insoluble powders and/or fibres may be included to improve dry slip or for the absorption of moisture, such as talc for the former and starch for the latter.

Various antimicrobial agents may also be included to enhance deodorant action, These include glyceryl monolaurate, propyl p-hydroxybenzoate, chlorhexidine gluconate, sodium lactoyl caprylate, benzyl alcohol, imidazolidinyl urea, trichlorocarbonilide, and zinc undecylenate, In addition, colors and fragrances may be added.

SPECIFIC DESCRIPTION OF THE INVENTION

The following examples illustrate the invention, In all instances, the sticks are attractive, transfer readily to the underarm, provide good deodorant action and are non-irritating. Identical compositions prepared with a coarser grade of sodium bicarbonate, in which 23% by weight was retained on a 325 mesh sieve, were found to be irritating by at least one-third of a test panel consisting of 12 subjects.

EXAMPLE 1

| | Parts By Weight |
|---|---|
| Decamethylcyclopentasiloxane (B,P, 380 F.) | 48.5 |
| Starch | 5.0 |
| Sodium bicarbonate, 100% through 325 Mesh | 17.0 |
| Stearyl alcohol | 21.2 |
| Cetyl alcohol | 2.0 |
| Hydrogenated coconut oil | 1.0 |
| Paraffin, M,P, 140/145 | 2.0 |
| Castorwax | 2.6 |
| Benzyl alcohol | 0.4 |
| Fragrance | 0.3 |

Melt the waxes in the silicone in a closed vessel at 85° C., Cool to 75° C. and add the starch while stirring, Add the sodium bicarbonate at 63° C., Continue stirring while cooling to 55° C., Add the benzyl alcohol and fragrance, Pour into containers at 54° C.

EXAMPLE 2

| | |
|---|---|
| Cyclic dimethylsiloxanes Mixt, D4, D5, D6 B,P, 360° F. | 50.0 |
| Stearyl alcohol | 26.3 |
| polyethylene glycol 400 distearate | 1.0 |
| Sorbitan monooleate | 2.0 |
| Sodium bicarbonate, 100% through 325 mesh | 17.5 |
| Starch | 2.5 |
| Glyceryl monolaurate | 0.4 |
| Fragrance | 0.3 |

Combine all ingredients, except for the starch, sodium bicarbonate and fragrance, Heat with stirring in a closed container to 65° C., After the fatty materials have melted, cool to 63° C. and stir in the starch and sodiuim bicarbonate, Cool to 53° C. and add the fragrance, Pour into containers at 48° C.

EXAMPLE 3

| | Parts By Weight |
|---|---|
| Ozokerite wax | 21.0 |
| Sodium bicarbonate, 100% through 325 mesh | 18.0 |
| Starch | 9.0 |
| Decyl oleate | 51.7 |
| Fragrance | 0.3 |

Combine the ozokerite wax with the decyl oleate, heat to 85° C. and maintain until the wax has melted, Cool to 75° C., mix in the other ingredients and pour into containers at 72° C.,

EXAMPLE 4

| | Parts By Weight |
|---|---|
| Paraffin Wax, M.P., 150/155 | 21.0 |
| Castorwax | 2.0 |
| Sodium bicarbonate, 100% through 325 mesh | 18.0 |
| Starch | 9.0 |
| Diisopropyl adipate | 59.7 |
| Fragrance | 0.3 |

Combine the wax with the adipate, heat to 85° C. to melt the waxes, Add the remaining ingredients at 70° C., mix well and pour into containers at 72° C.

EXAMPLE 5

| | Parts By Weight |
|---|---|
| Castorwax | 2.0 |
| Paraffin Wax, M.P. 150/155 | 3.7 |
| Stearyl alcohol | 22.2 |
| Sodium bicarbonate, 100% through 325 mesh | 18.0 |
| Starch | 7.0 |
| Light mineral oil 52/57 SUS @ 100° F. | 27.8 |
| Decamethylcyclopentasiloxane, B,P, 380° F. | 18.5 |
| Benzyl alcohol | 0.5 |
| Fragrance | 0.3 |

Combine the waxes with the mineral oil and silicone, Heat to 80° C. to melt the waxes and cool to 65° C., Add the remaining ingredients, mix well and pour into containers at 58° C.

We claim:

1. In an essentially anhydrous underarm deodorant stick comprising from about 30 to 80% by weight of a water-insoluble organic liquid, from about 10 to about 40% by weight of an organic gelling agent, and from about 10 to about 40% by weight of a powdered sodium bicarbonate suspended in the gelled vehicle the aforementioned percentage by weights based on the weight of the total composition the improvement being the powdered sodium bicarbonate has a particle size in the range of essentially 100% less than 44 microns and at least about 25% greater than 1 micron the particle size of the powdered sodium bicarbonate being sufficiently small so as to avoid irritation due to abrasion, but not so small as to interfere with the easy glide of the stick.

2. In an underarm deodorant stick according to claim 1 wherein from 25 to 100% by weight of the water-insoluble organic liquid is a volatile liquid boiling within the range of 300° F. to 500° F. and selected from the group consisting of saturated aliphatic hydrocarbons, linear polydimethylsiloxanes and polydimethylcyclosiloxanes.

3. In an underarm deodorant stick according to claim 1 wherein at least about 25% of the gelling agent is a long chain aliphatic alcohol having 16 to 22 carbon atoms in the chain.

* * * * *